(12) United States Patent
Yamada

(10) Patent No.: US 8,359,180 B2
(45) Date of Patent: Jan. 22, 2013

(54) THERMAL ANALYSIS APPARATUS

(75) Inventor: Kentaro Yamada, Chiba (JP)

(73) Assignee: SII NanoTechnology Inc. (JP)

( * ) Notice: Subject to any disclaimer, the term of this patent is extended or adjusted under 35 U.S.C. 154(b) by 321 days.

(21) Appl. No.: 12/806,997

(22) Filed: Aug. 25, 2010

(65) Prior Publication Data

US 2011/0054829 A1  Mar. 3, 2011

(30) Foreign Application Priority Data

Sep. 1, 2009 (JP) ................................. 2009-202092

(51) Int. Cl.
*G01K 17/00* (2006.01)
*G06F 15/00* (2006.01)
(52) U.S. Cl. ......................... 702/136; 702/130; 374/127
(58) Field of Classification Search .................... 702/99, 702/130, 131, 132, 136; 374/120, 127, 161; 600/438
See application file for complete search history.

(56) References Cited

U.S. PATENT DOCUMENTS 5,893,051 A * 4/1999 Tomohiro ..................... 702/130
7,416,330 B2 * 8/2008 Ito et al. ........................ 374/127

OTHER PUBLICATIONS

Patent Abstracts of Japan, publication No. 08-327573, publication date Dec. 13, 1996.
Patent Abstracts of Japan, publication No. 2001-033410, publication date Feb. 9, 2001.
Patent Abstracts of Japan, publication No. 2001-183319, publication date Jul. 6, 2001.

* cited by examiner

*Primary Examiner* — John H Le
(74) *Attorney, Agent, or Firm* — Adams & Wilks

(57) ABSTRACT

To avoid an influence on measurement accuracy in a case where an observation window for a measurement sample is provided to a thermal analysis apparatus, the influence being imposed by thermal conduction through the observation window, the observation window is formed of layers of transparent members, and a gap layer is provided between the layers, to thereby reduce the thermal conduction. Gas or solid having a high heat insulation property is employed for the gap layer to further enhance a heat insulation property of the observation window. Accordingly, a change due to heating of the measurement sample is visually observed in the thermal analysis apparatus, to thereby obtain a thermal change or a physical change with higher accuracy.

6 Claims, 3 Drawing Sheets

THERMAL ANALYSIS APPARATUS

BACKGROUND OF THE INVENTION

1. Field of the Invention

The present invention relates to a thermal analysis apparatus capable of measuring a thermophysical property of a sample, which changes along with a temperature change, and of imaging and displaying the sample.

2. Description of the Related Art

Among the thermal analysis apparatus, a differential scanning calorimeter is a thermal analysis apparatus in which temperatures of a sample and a reference substance received within a furnace are changed based on a constant rate program, and a temperature difference between the sample and the reference substance is detected, thereby measuring the temperature difference to obtain a heat flow difference. There is known an apparatus which is obtained by combining the differential scanning calorimeter as described above with means for imaging the sample within the furnace, and which records an image of a change in sample state as image data along with a change in heat quantity of a sample under measurement, to thereby enable a change in sample substance to be analyzed in more detail (Japanese Patent Application Laid-open No. Hei 08-327573).

In Japanese Patent Application Laid-open No. Hei 08-327573, one layer of a transparent observation window made of quartz glass is newly provided to a lid portion in the upper part of the furnace generally constructed of a non-transparent metal material or the like, and further, imaging means for imaging a sample within the furnace is combined therewith, to thereby record a sample state at the time when temperature rises and drops as image data along with a DSC curve. This enables a change in sample state to be grasped correctly, which is difficult to determine based only on the DSC curve.

Further, there is provided a differential scanning calorimeter including the same imaging means, which has transparent observation windows provided not only to the lid of the furnace but also to the upper part of a furnace cover that covers the periphery of the furnace, and in which purge gas is supplied to the transparent observation windows to suppress dewing and frosting occurring on the observation windows in a low temperature range (Japanese Patent Application Laid-open No. 2001-183319).

Further, there is disclosed a differential thermal analysis apparatus including a sample cylinder for receiving a reference substance and a sample, and a side wall of an outer cylinder thereof, which are made of a transparent material, to thereby visually recognize the state within the sample cylinder (Japanese Patent Application Laid-open No. 2001-33410).

It is preferred that the lid portion of the furnace of the thermal analysis apparatus have high thermal conductivity and an even temperature state, originally. However, in the thermal analysis apparatus described in Japanese Patent Application Laid-open No. Hei 08-327573, the transparent observation window, which is used for observing a sample and is provided to the lid in the upper part of the furnace, is made of quartz glass, and hence the thermal conductivity is poor and uneven temperature distribution is likely to be generated in the window portion due to an influence of disturbance of the environment outside the furnace. Further, the transparent observation window is formed of one layer, and hence the above-mentioned uneven temperature distribution generated in the observation window may easily be spread to the inside of the furnace, with the result that the influence of the disturbance may easily be imposed on temperature distribution within the furnace and temperature distribution of gas within the furnace. Meanwhile, a differential heat flow detection portion installed in the furnace has high sensitivity so as to detect a minute temperature difference between the sample and the reference substance. Therefore, the differential heat flow detection portion may detect, as a signal, the influence of the disturbance imposed on the temperature of the furnace lid, the temperature within the furnace, or the temperature of the gas within the furnace with high sensitively via solid thermal conduction and gas thermal conduction, or radiation. As a result, the uneven temperature distribution generated by the disturbance of the environmental temperature in the transparent observation window formed of one layer may cause distortion, fluctuation, and the like in the DSC curve. This leads to a problem that it is difficult to obtain a stable and accurate DSC curve.

As to the technology described in Japanese Patent Application Laid-open No. 2001-183319, transparent observation windows are provided not only to the furnace lid but also to the upper part of the furnace cover that covers the furnace, which means that two layers of transparent windows are provided. However, though the furnace is required to ensure a stable temperature distribution under precise temperature control for a thermal analysis/measurement, the observation window of the furnace lid provided to the upper part of the furnace portion is formed of one layer, which leads to the same problem as in Japanese Patent Application Laid-open No. Hei 08-327573.

Also in Japanese Patent Application Laid-open No. 2001-33410, the transparent material portion formed in the side wall of the sample cylinder is formed of one layer, which leads to the same problem.

SUMMARY OF THE INVENTION

In view of the above, the present invention has been made in order to solve the problem with the thermal conductivity of the transparent observation window provided to the lid portion of the furnace, and it is therefore an object of the present invention to provide a thermal analysis apparatus which includes a transparent observation window and imaging means that are used for observing a sample state within a furnace, and is capable of obtaining excellent thermal analysis data with less distortion and fluctuation.

In order to achieve the above-mentioned object, a thermal analysis apparatus according to the present invention includes: a furnace including a receiving portion for receiving a measurement sample; a detection portion for measuring, in a state in which the measurement sample is placed in the furnace, a thermal change generated in the measurement sample when temperature within the furnace rises and drops; sample imaging means for imaging the measurement sample placed in the furnace; thermal analysis data collection means for collecting data of a thermal analysis obtained by recording a change in heat quantity among the physical quantity; image data collection means for collecting image data obtained by imaging the measurement sample at the same time when a thermal analysis is performed; and thermophysical property analysis display means for one of recording and displaying, as information to be used for a thermophysical property analysis for the measurement sample, the thermal analysis data collected by the thermal analysis data collection means and the image data collected by the image data collection means, in which: at least a part of a wall portion of the furnace in a range in which observation of the measurement sample is possible is formed of a transparent member; the transparent member comprises at least two layers; and a space between the at least two layers is a heat insulation layer. Accordingly, the present invention relates to all types of thermal analysis apparatus.

For the transparent observation window formed in at least the part of the furnace, a transparent material having heat resistance and rigidity, such as quartz glass and borosilicate glass, may be used. The observation window formed of the transparent material includes at least two layers, and hence temperature disturbance due to temperature of gas outside the furnace within the apparatus directly and mainly influences the transparent member of a furnace outer layer that constitutes the transparent observation window. In addition, the heat insulation layer provided between the transparent members produces an effect of preventing the influence of the uneven temperature distribution generated in the above-mentioned transparent member of the furnace outer layer from being spread to the transparent member of a furnace inner layer. Accordingly, the influence of the disturbance on the temperature distribution within the furnace and the temperature distribution of the gas within the furnace may be suppressed to a low level. As a result, a stable temperature distribution is ensured within the furnace because of the smaller influence of the disturbance, and the detection portion for the thermal change, which is installed within the furnace, does not detect the influence of the disturbance as a signal. Thus, stable and accurate detection for a thermal change and imaging of a sample state at the time of the detection are enabled.

Note that, the transparent member and the heat insulation layer may be designed as appropriate with regard to an area, thickness of the member, and an interlayer distance in accordance with the specification of the thermal analysis apparatus to be used, as long as the effect of the present invention is obtained.

As described above, according to the present invention, the transparent observation window provided to the part of the furnace lid to allow the sample state to be imaged includes at least two layers, and the layer having a heat insulation effect is provided between the transparent members, which reduces the risk that the influence of the temperature disturbance outside the furnace becomes a factor of instability with respect to the temperature within the furnace. As a result, the case where the influence of the temperature disturbance is detected by the detection portion for the thermal change, which is installed within the furnace, is avoided, to thereby build an environment for measuring a thermal change in a sample with no disturbance. As a result, stable and accurate thermal analysis data can be obtained with less distortion and fluctuation.

DETAILED DESCRIPTION OF THE PREFERRED EMBODIMENT

Hereinbelow, an embodiment of the present invention is described in detail with reference to the accompanying drawings. Note that, in this embodiment, repetitive description may be omitted for components with similar description.

Embodiment

Figure 1:
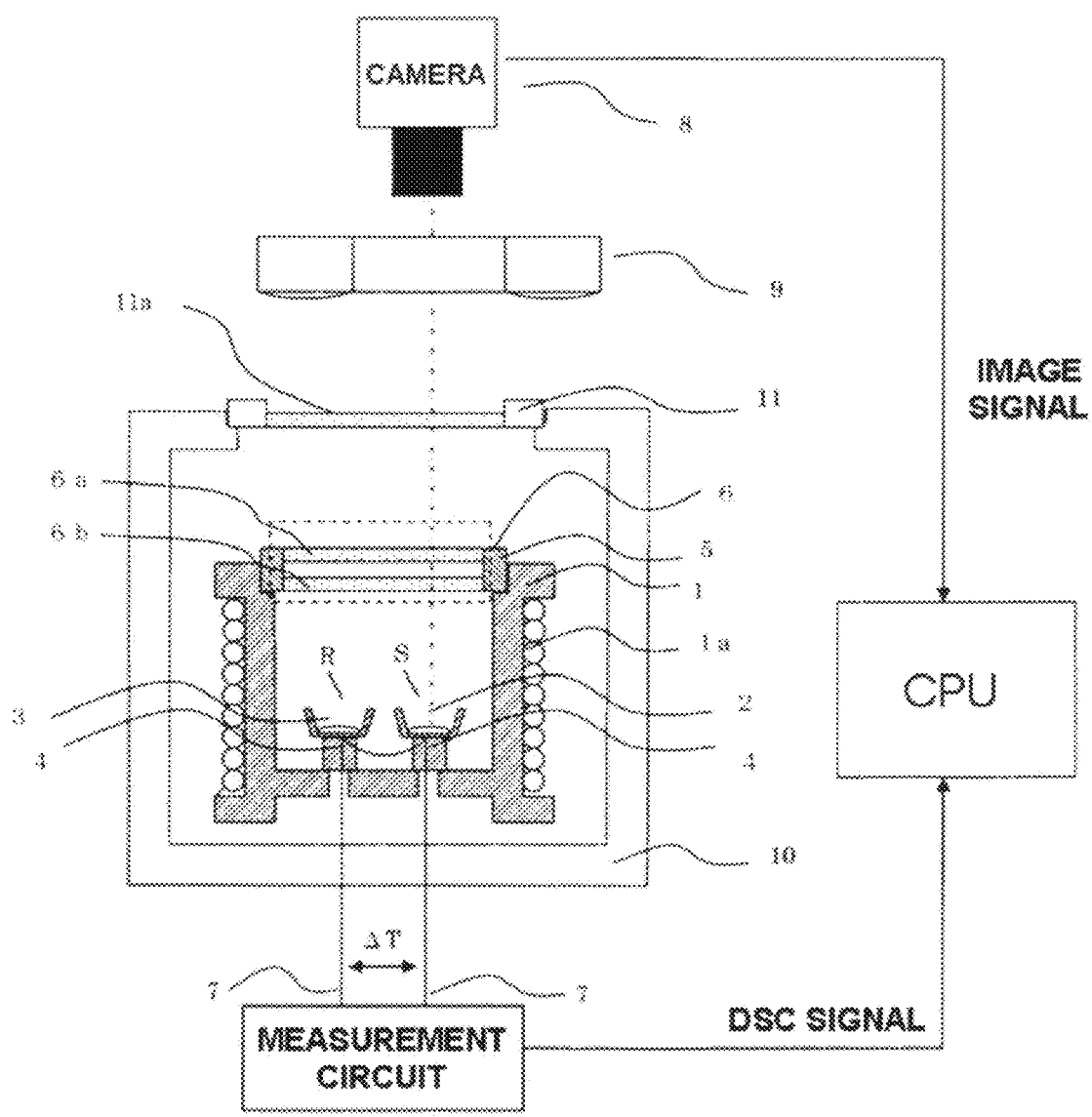
FIG. 1 is a configuration diagram according to an embodiment of the present invention.

FIG. 1 illustrates a configuration of a differential scanning calorimeter (DSC) as an example of a thermal analysis apparatus according to the present invention. The differential scanning calorimeter includes a furnace 1 and a heater coil 1a wound therearound. The heater coil 1a is used for heating the furnace 1. Although not illustrated, the furnace 1 has a cover attached therearound so that the heater coils 1a are not exposed. There are arranged, within the furnace 1, a sample holder 2 for receiving a measurement sample and a reference sample holder 3 for receiving a reference sample. The respective holders have thermocouples connected thereto, which constitute differential heat flow detection portions 4 for detecting a temperature difference between the holders. Thermocouple wires 7 extending from the differential heat flow detection portions 4 are connected to a measurement circuit, and detected signals are recorded in the form of a DSC curve after being amplified.

The furnace 1 has a furnace lid 5 detachably arranged on the upper part thereof. The furnace lid 5 includes a transparent observation window portion 6 for observing the sample. There is arranged, around the furnace 1, a furnace cover 10 so as to cover the entire furnace 1, and a furnace cover lid 11 provided in the upper part thereof also includes a transparent observation window 11a. With this configuration, the state of the sample placed in the furnace can be observed from above the differential scanning calorimeter.

Figure 2:
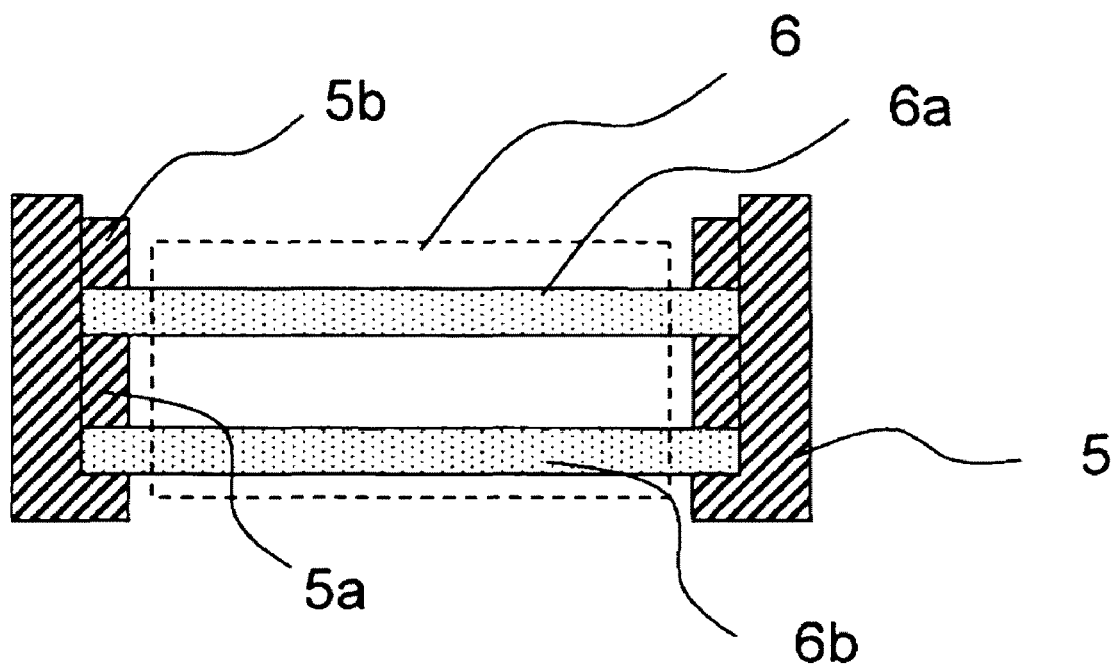
FIG. 2 is a configuration diagram of a furnace lid according to the embodiment of the present invention.

FIG. 2 is a configuration diagram of the furnace lid 5. The furnace lid 5 is formed of a material having excellent thermal conductivity, such as aluminum, and has a through hole in a part of the center thereof. A transparent member such as quartz glass is inserted into the through hole as an observation window, which constitutes the transparent observation window portion 6. The transparent observation window portion 6 is constituted by two transparent members (transparent member 6a and transparent member 6b), which sandwich a spacer 5a for securing a gap layer between the layers, and is attached to the furnace lid 5 with a window holding member 5b. The gap layer is a gas layer, in which thermal conductivity of gas is lower than thermal conductivity of normal solid, and hence the transparent observation window portion 6 serves as a heat insulation layer having a heat insulation property, which further suppresses thermal conduction as compared with the case where the transparent observation window portion 6 is formed of one layer.

Note that, the gap layer may be another layer other than the gas layer as long as the gap layer is transparent enough to observe the sample and has a characteristic that can provide a heat insulation property for blocking an influence of disturbance. For example, the gap layer may have a vacuum inside, or may be formed of a solid or liquid material having lower thermal conductivity than quartz glass or the like has.

In addition to the above-mentioned configuration, the differential scanning calorimeter includes a camera 8 for imaging the sample placed in the furnace 1, and a lighting 9 for securing brightness necessary for the imaging, the camera 8 and the lighting 9 being arranged above the transparent observation window portion 6 provided to the furnace lid 5 and the transparent observation window 11a provided to the furnace cover lid 11. The differential scanning calorimeter further includes data processing means capable of displaying and storing an image signal from the camera 8 as image data.

Figure 3:
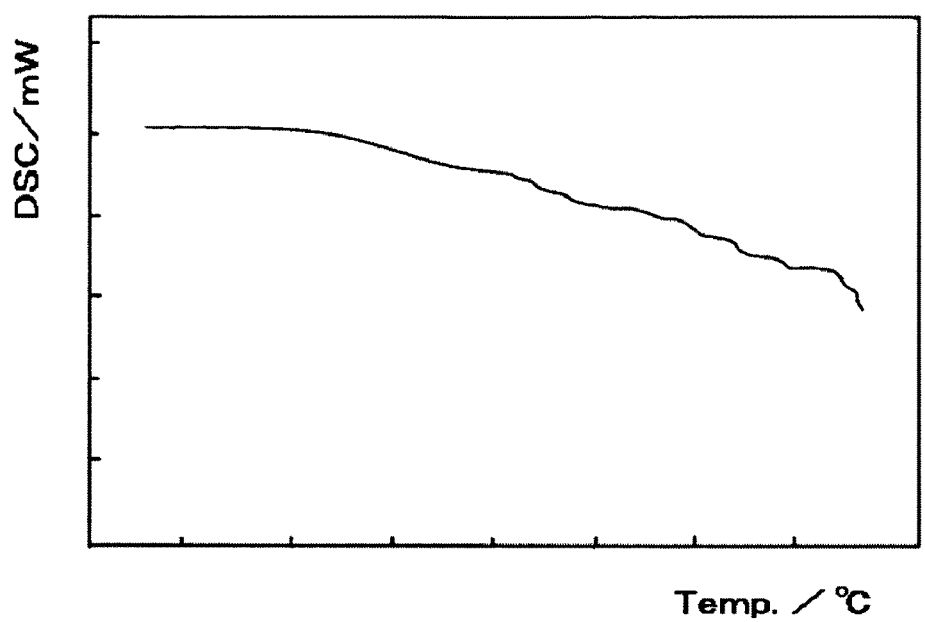
FIG. 3 is a graph showing an example of a conventional DSC curve.
Figure 4:
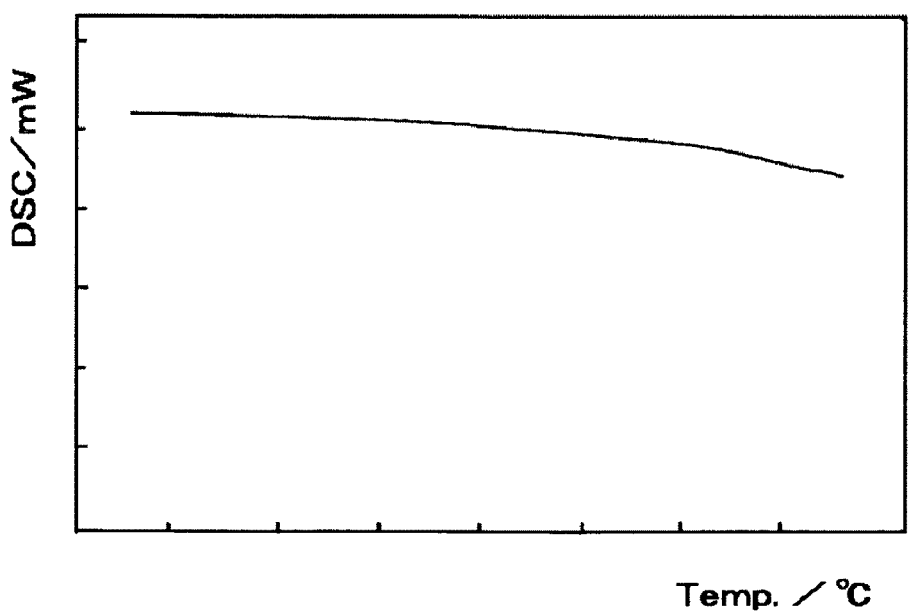
FIG. 4 is a graph showing an example of a DSC curve of an apparatus according to the embodiment of the present invention.

FIGS. 3 and 4 each illustrate detection results of differential heat detected as thermal change in the above-mentioned configuration. FIG. 3 is a graph showing a measurement example of a DSC curve obtained in the case where the transparent observation window portion is formed of one layer. FIG. 4 is a graph showing a measurement example of a DSC curve obtained in the case where the transparent observation window portion 6 is formed of two layers. FIGS. 3 and 4 each have the axis of ordinate representing heat flow differences and the axis of abscissa representing temperature, and show an example in which temperature rises at a constant rate. Note that, the respective axes have the same scale.

In the configuration of FIG. 3, in which the transparent observation window portion is formed of one layer, the DSC curve is bent and has fluctuations as the temperature rises. In contrast, in the configuration of FIG. 4 according to the present invention, in which the transparent observation window portion is formed of two layers and the heat insulation layer formed of gas is provided between the transparent members, the bending and fluctuations are reduced. It is obvious from the above-mentioned results that, when the transparent observation window portion 6 to be provided to the furnace lid 5 of the differential scanning calorimeter has the configuration according to the present invention, the smaller influence of thermal disturbance is imposed on the differential heat flow detection portions arranged within the apparatus. Accordingly, stable results can be obtained.

Note that, the above-mentioned embodiment has exemplified the case of the differential scanning calorimeter, but the present invention is applicable to a thermomechanical analysis (TMA) or a dynamic mechanical analysis (DMA), which requires no reference sample, or a thermogravimetry (TG) or a differential thermal analysis (DTA), which requires a reference sample, as the thermal analysis apparatus that avoids the influence of thermal disturbance, which is the gist of the present invention.

What is claimed is:

1. A thermal analysis apparatus, comprising:
   a furnace comprising a first receiving portion for receiving a measurement sample;
   a detection portion for measuring, in a state in which the measurement sample is placed in the furnace, a physical quantity generated in the measurement sample when temperature within the furnace rises and drops;
   sample imaging means for imaging the measurement sample placed in the furnace;
   thermal analysis data collection means for collecting data of a thermal analysis obtained by recording a change in heat quantity among the physical quantity;
   image data collection means for collecting image data obtained by imaging the measurement sample at the same time when the thermal analysis is performed; and
   thermophysical property analysis display means for one of recording and displaying, as information to be used for a thermophysical property analysis for the measurement sample, the thermal analysis data collected by the thermal analysis data collection means and the image data collected by the image data collection means, wherein:
   at least a part of a wall portion of the furnace in a range in which observation of the measurement sample is possible is formed of a transparent member;
   the transparent member comprises at least two layers; and
   a space between the at least two layers is a heat insulation layer.

2. A thermal analysis apparatus according to claim 1, wherein the heat insulation layer comprises gas.

3. A thermal analysis apparatus according to claim 1, wherein the furnace further comprises a second receiving portion for receiving a reference sample.

4. A thermal analysis apparatus according to claim 3, wherein the detection portion detects a differential heat flow between the measurement sample and the reference sample.

5. A thermal analysis apparatus according to claim 3, wherein the detection portion detects a relative change in weights of the measurement sample and the reference sample, which is generated along with a change in ambient temperature.

6. A thermal analysis apparatus according to claim 1, wherein the detection portion detects a quantity of a change in length of the measurement sample.

* * * * *